United States Patent [19]

Bugaut et al.

[11] 4,125,601
[45] Nov. 14, 1978

[54] SUBSTITUTED NITROAMINOPHENOLS, PROCESS FOR THEIR PREPARATION AND DYEING COMPOSITIONS IN WHICH THEY ARE PRESENT

[75] Inventors: Andree Bugaut, Boulogne; Monique Andrillon, Aulnay-sous-Bois, both of France

[73] Assignee: L'Oreal, Paris, France

[21] Appl. No.: 789,444

[22] Filed: Apr. 20, 1977

[30] Foreign Application Priority Data

Apr. 21, 1976 [LU] Luxembourg .......................... 74807

[51] Int. Cl.$^2$ ..................... A61K 7/09; A61K 7/13; C07C 91/06
[52] U.S. Cl. ..................................... 424/71; 8/10.1; 8/10.2; 260/573; 260/456 R; 562/22
[58] Field of Search ................... 260/573; 8/10.2, 10.1; 424/71

[56] References Cited

U.S. PATENT DOCUMENTS 3,344,031  9/1967  Bartoszewicz .................... 260/573
4,007,228  2/1977  Kalopissis et al. ................ 260/573

Primary Examiner—Sam Rosen
Attorney, Agent, or Firm—Brisebois & Kruger

[57] ABSTRACT

Chemical compounds of the formula:

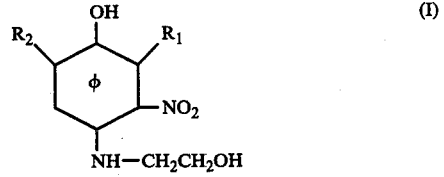

in which $R_1$ and $R_2$ can be identical or different and represent hydrogen or alkyl having from 1 to 4 carbon atoms. The compounds are used in hair dyeing, and a process for their preparation is disclosed.

21 Claims, No Drawings

SUBSTITUTED NITROAMINOPHENOLS, PROCESS FOR THEIR PREPARATION AND DYEING COMPOSITIONS IN WHICH THEY ARE PRESENT

It is known that, in dyeing compositions for keratin fibres and in particular for hair, red tints are necessary as the base for the production of dyeings corresponding to the mahogany and coppery shades. It is desirable that the dyestuffs which can give these tints can be used as a mixture with oxidation dyestuffs to give permanent dyeings, which requires that they must, necessarily, be stable in the presence of hydrogen peroxide in ammoniacal solution.

The object of the present invention is to propose a direct dyestuff which corresponds to the conditions indicated above.

The present invention relates to the new industrial product which consists of a chemical compound of the formula:

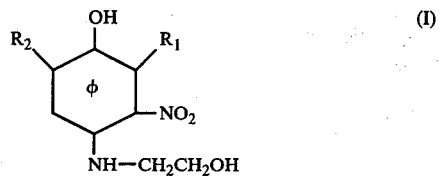

in which formula $R_1$ and $R_2$ are identical or different and represent hydrogen or alkyl having from 1 to 4 carbon atoms.

The chemical compound of the formula (I) is a coloured molecule, which can be used to dye keratin fibres and, in particular, human hair.

Specific examples of some chemical compounds which are encompassed by the above formula and which are contemplated by the present invention are: 3-nitro-4β-hydroxyethylamino-phenol; 2-methyl-4β-hydroxyethylamino-5 nitro-phenol; 2,6 dimethyl-4β-hydroxyethylamino-3 nitro-phenol.

Similar chemical compounds having colouring properties which can be used for the dyeing of hair have already been described, in the prior art.

A positional isomer of the compounds of the formula (I), namely 2-(N-β-hydroxyethyl-amino)-4-nitro-phenol, has been described for hair dyeing in French Pat. No. 1,051,605. This compound imparts a yellow coloration to keratin fibres, that is to say it cannot make it possible to obtain the red coloration which is necessary in formulations and which is obtained with the compounds of the formula (I).

The preparation of another positional isomer of the compounds of the formula (I) has been described in British Pat. No. 1,012,793, but this product is used as a starting material in synthesis without it being indicated that it is useful for the dyeing of keratin fibres. This positional isomer is 2-(N-β-hydroxyethylamino)-5-nitro-phenol which, when it is used for the dyeing of hair, produces a green-yellow coloration, so that it is not possible to obtain the red coloration which is necessary, in formulations, to obtain coppery or mahogany shades, or more or less reddish chestnut shades.

Furthermore, the method of preparation described for these two isomers consists of reacting glycol chlorohydrin directly with the amine group. This method of preparation does not apply to the preparation of the compounds of the formula (I), in which the amine group in the position ortho to the $NO_2$ group is not sufficiently reactive. Moreover, this method of preparation has disadvantages which are not inconsiderable: thus, by the action of glycol chlorohydrin on 3-nitro-4-amino-phenol, according to the process described in Example 1 of British Pat. No. 1,012,793, about 50% of the starting material is recovered after heating for 5 hours and, moreover, a side reaction takes place at the same time as the expected reaction.

In the series of known nitro-amino-phenols, only 3-nitro-4-N-methylamino-phenol, which is described in the publication J. Chem. Soc. (C) 1967, page 1056, imparts a red coloration to keratin fibres, analogous to that obtained by the compounds of the formula (I). However, the advantages provided for hair dyeing, by substituting the amine groups by β-hydroxyl-$CH_2$—$CH_2OH$ groups in the benzenoid nitro dyestuffs series, have been stated in several prior patents. Furthermore, the synthesis of the N-methyl derivative is difficult to apply industrially since it necessitates a reaction in anhydrous benzene and repeated extractions with ether. Moreover, the process used for the manufacture of this compound does not apply to the synthesis of the compounds of the formula (I).

It has been found that the compounds of the formula (I) benefit from a good solubility in the solvents generally used in hair dyeing, which makes it possible to use them at a fairly high concentration in order to impart a powerful and lustrous red coloration, with good harmony, to the keratin fibre. The dyeing obtained exhibits a good stability to light and to weather. In addition, the use in hair dyeing of the compounds of Formula (I), are characterized by their being very harmless.

The present invention therefore also relates to the new industrial product which consists of a dyeing composition for keratin fibres, and in particular for hair, characterised in that it comprises, in aqueous solution, at least one compound of the formula (I).

It is to be noted that, in the series of benzenoid nitro dyestuffs, it is unusual to be able to benefit at one and the same time, as is the case for the dyeing compositions defined above, from the double advantage that a good quality red coloration is obtained and that the dyeing compositions in question are harmless when applied.

Furthermore, the dyeing compositions which contain the compounds of the formula (I) are particularly valuable since the said compounds of the formula (I) benefit from a good stability, in ammoniacal solution, towards hydrogen peroxide, which makes it possible to introduce oxidation dyestuffs into the dyeing compositions of this invention.

In a preferred embodiment, the dyeing composition of this invention contains 0.002% to 5% by weight of at least one compound of the formula (I); the pH of the composition is between 3 and 11 and, preferably, between 8 and 10; the pH of the composition is established by organic amines or by ammonia; monoethanolamine, diethanolamine and triethanolamine should be mentioned amongst the organic amines which can be used, and it is also possible to use sodium hydrogen phosphate as the agent for rendering the composition alkaline.

The coloured compounds of the formula (I) can be used in so-called semi-permanent dyeing compositions, alone or as a mixture with other coloured compounds, called direct dyestuffs, that is to say dyestuffs which can, by themselves, impart a coloration to keratin fibre without the use of an oxidising agent. They can, in particular, be present in these semipermanent dyeing compositions as a mixture with other known nitro dyestuffs of the benzenoid series, having the general formula (II):

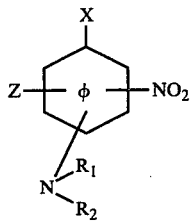
(II)

in which formula X represents either hydrogen, halogen or alkyl, or

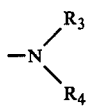

or OR$_5$, with R$_1$, R$_2$, R$_3$, R$_4$ and R$_5$, which may be identical or different, being hydrogen, alkyl or a substituted alkyl such as a hydroxyalkyl, aminoalkyl, acylaminoalkyl, carbethoxyaminoalkyl, ureidoalkyl, carboxyalkyl, sulphoalkyl, carbamylalkyl, methoxyalkyl or mesylaminoalkyl, and Z represents hydrogen or halogen, or alkyl or alkoxy or NO$_2$. The compounds of the formula (I) can also be mixed, in the semi-permanent dyeing compositions, with anthraquinone dyestuffs, azo dyestuffs, oxazines, indoanilines and indophenols.

The compounds of the formula (I) can also be used as a mixture with other direct dyestuffs in colouring wave-setting lotions which are, in general, aqueous-alcoholic solutions containing one or more well known cosmetic resins such as polyvinylpyrrolidone sold under code N K30 by the "General Aniline and Film Corporation"; a copolymer of vinyl acetate and crotonic acid (90% vinyl acetate, 10% crotonic acid; molecular weight = 45,000 to 50,000)

As has been indicated above, the compounds of the formula (I) are stable in ammoniacal solution in the presence of hydrogen peroxide, that is to say the colour that they impart to the keratin fibre is not destroyed by an oxidising agent. It is therefore possible to use the compounds of the formula (I) in so-called oxidation dyeing compositions, that is to say which necessitate the simultaneous application of oxidising agents in order to bring about the development of the desired colour. In effect, it is known that the addition of direct dyestuffs to so-called oxidation dyes is often used to obtain tints with a richer sheen or to improve the harmony. It will therefore be possible to use the compounds of the formula (I) as mixtures with the two classes of coloration precursors, that is to say with oxidation bases (or "para compounds") and with couplers. The para-phenylenediamine or para-aminophenol oxidation bases which can be used mixed with the compounds of the formula (I) in oxidation dyeing compositions can advantageously have the general formula:

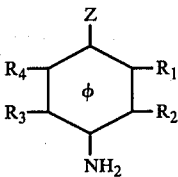
(III)

in which formula R$_1$, R$_2$, R$_3$ and R$_4$ are identical or different and represent hydrogen, alkyl, alkoxy or halogen, Z represents OH or

R$_5$ and R$_6$ being identical or different and representing hydrogen, alkyl or a substituted alkyl such as a hydroxyalkyl, carbamylalkyl, mesylaminoalkyl, acylaminoalkyl or sulphoalkyl, with the reservation that R$_1$ and R$_4$ represent hydrogen when the R$_5$ and R$_6$ do not represent hydrogen. It will also be possible for the oxidation bases to contain a heterocyclic ring, as is the case, for example, with 2,5-diaminopyridine or 2-amino-5-hydroxy-pyridine. The couplers, which can be present in the dyeing compositions according to the invention which contain oxidation bases, can advantageously be chosen from the group consisting of:

(a) α-naphthol, resorcinol and its derivatives which are substituted in the nucleus, for example chlororesorcinol, orcinol or cresorcinol, (b) the meta-aminophenols which are substituted in the nucleus or on the amine group and which correspond to the general formula

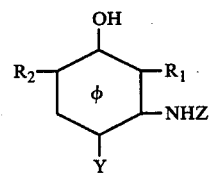
(IV)

in which formula R$_1$ and R$_2$ can be identical or different, and represent hydrogen, alkoxy, alkyl or halogen, Y represents hydrogen, alkoxy or alkyl, and Z represents alkyl, substituted alkyl such as hydroxyalkyl or carbamylalkyl, or acyl, ureido or carbethoxy group, with the reservation that R$_2$ must be hydrogen and Z must be hydrogen or alkyl or substituted alkyl when Y is an alkyl, (c) the metadiamines, which can have substituents in the nucleus or on the amine group, such as 2,4-diaminoanisole or 3-(N-β-hydroxyethylamino)-aniline, (d) the couplers which comprise a pyridine nucleus such as 2,6-diamino-pyridine and 2-amino-6-hydroxy-pyridine, and (e) the couplers of the group of pyrazolones, β-diketones and 6-hydroxy-phenomorpholine.

It will also be possible for the dyeing compositions according to the invention to contain one or more auto-oxidisable hair dyestuffs, that is to say chemical compounds which can impart a coloration to keratin fibres by simple oxidation in air, and, in particular, trihydroxybenzene, diaminophenol, triaminophenol, the aminodiphenols and the diaminodiphenols, as well as derivatives of these compounds which are substituted in the nucleus or on the amine groups, or the leuco-derivatives of indoaniline or of indophenol.

The dyeing compositions according to the invention can, in addition, contain solvents other than the water which is always present in dyeing compositions, and in particular, ethanol, isopropanol, ethylene glycol and the monomethyl ether of ethylene glycol, anionic, cationic or non-ionic surface-active agents, sulphonated esters of alcohol (sic), sulphates of fatty alcohols and sodium lauryl-sulphate, thickeners such as carboxymethylcellulose or acrylic polymers, antioxidants such as sodium sulphite or thioglycollic acid, sequestering agents such as ethylenediaminetetraacetic acid, and perfumes.

Finally, the present invention relates to a new manufacturing process which makes it possible to obtain the compounds of the formula (I) with a good yield. It is to be noted that this manufacturing process can easily be applied to industrial production lines and, as a consequence, the cost price of the compound of the formula (I) is comparatively low. The starting material, which makes it possible to manufacture the compounds of the formula (I), is a 3-nitro-4-amino-phenol, optionally substituted in the 2-and 6-positions by an alkyl group. The preparation of such a compound can be carried out according to the process described in U.S.S.R. Pat. No. 380,640.

The manufacturing process according to the invention is characterised in that chloroethyl chloroformate is reacted with 3-nitro-4-amino-phenol, optionally substituted in the 2-and/or 6-position(s) by an alkyl radical containing 1 to 4 carbon atoms, the reaction taking place in dioxane in the presence of calcium carbonate, and in that alkaline hydrolysis of the carbamate which is formed is carried out thereafter.

In a preferred embodiment, the action of the chloroethyl chloroformate takes place at a temperature of between about 70 and 100° C.; the alkaline hydrolysis of the carbamate which is formed takes place in a concentrated aqueous solution of potassium hydroxide at a temperature of about 0° C.

In order that the subject of the invention shall be better understood, several embodiments of the manufacturing process according to the invention and several examples of dyeing compositions using the compound of the formula (I) will now be described, without implying a limitation.

EXAMPLE 1: Preparation of 3-nitro-4-(β-hydroxyethylamino)phenol.

This process comprises two stages which are represented by the following reaction equations:

1st stage:

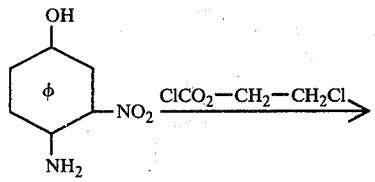

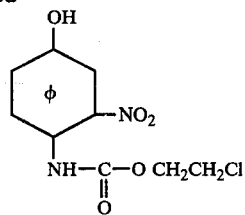

2nd stage:

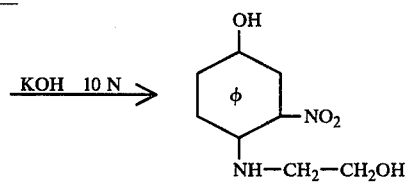

1st stage: Preparation of β-chloroethyl N-[(2-nitro-4-hydroxy) phenyl] carbamate.

0.3 mol (45g) of 3-nitro-4-amino-phenol (melting point = 151° C.), prepared as indicated in the state of the art, is dissolved in 135 ml of dioxane. 0.165 mol (16.5 g) of calcium carbonate is added. The mixture is heated to about 70° C. and then 0.33 mol (34.5 ml) of chloroethyl chloroformate is added little by little, with stirring. The reaction mixture is kept on a boiling water bath for 1 hour 30 minutes. The reaction mixture is filtered whilst hot. After cooling, the reaction mixture is poured on to 400 g of iced water. The expected product, which has precipitated, is filtered off and then washed with water. The melting point is 140° C. and the yield is 85%.

2nd stage: Preparation of 3-nitro-4-(β-hydroxyethyl-amino)phenol.

0.1 mol (26g) of β-chloroethyl N-[(2-nitro-4-hydroxy) phenyl]carbamate is introduced little by little, into 78 ml of 10 Normal potassium hydroxide solution with stirring and at ambient or room temperature. The reaction mixture is left for three hours at ambient temperature and then overnight at 0° C. The expected product, which has precipitated in the form of potassium phenate, is filtered off. The potassium phenate is dissolved in water and 3-nitro-4-(β-hydroxyethylamino)-phenol is precipitated by neutralising this aqueous solution using hydrochloric acid; this product, after filtering off, washing with water and recrystallisation from ethyl acetate, melts at 142° C. The yield is 90%.

Analysis of the product obtained gave the following results:

| Analysis | Calculated for $C_8H_{10}N_2O_4$ | Found |
|---|---|---|
| C % | 48.48 | 48.53 |
| H % | 5.09 | 5.19 |
| N % | 14.14 | 14.08 |

EXAMPLE 2: Preparation of 2-methyl-4-(β-hydroxyethylamino)-5-nitro-phenol.

This process comprises four stages which are represented by the following reaction equations:

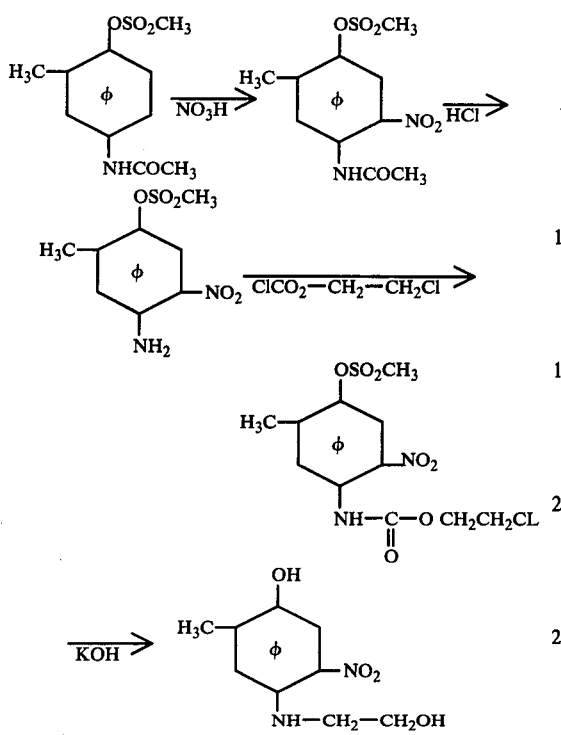

1st stage: Preparation of 2-methyl-4-acetoamino-5-nitromesyloxybenzene.

34 ml of nitric acid (d = 1.49) are added, at between 0° and 5° C., to 0.5 mol (121g) of 2-methyl-4-acetoamino-mesyloxybenzene (melting point = 96° C.) suspended in 250 ml of acetic anhydride. Stirring, at between 0° and 5° C., is maintained for one hour and then the reaction mixture is diluted with 2 l of iced water. The expected nitro derivative precipitates. It is filtered off, washed with water, recrystallised twice from ethanol and dried in vacuo. Its melting point is 119° C.

Analysis of the product obtained gave the following results:

| Analysis | Calculated for $C_{10}H_{12}N_2O_6S$ | Found |
|---|---|---|
| C % | 41.67 | 41.47 |
| H % | 4.20 | 4.25 |
| N % | 9.72 | 9.55 |
| S % | 11.10 | 11.03 |

2nd stage: Preparation of 2-methyl-4-amino-5-nitro-mesyloxybenzene.

0.43 mol (124 g) of 2-methyl-4-acetoamino-5-nitromesyloxybenzene, in 320 ml of hydrochloric acid (d = 1.18) to which 160 ml of acetic acid have been added, is heated for two hours on a boiling water bath. The reaction mixture is diluted with one liter of water. The expected product crystallises. This product is washed with water and dried in vacuo. It melts at 128° C.

3rd stage: Preparation of β-chloroethyl N-[(2-nitro-4-mesyloxy-5-methyl)phenyl]carbamate.

0.215 mol (21.5g) of calcium carbonate and 0.43 mol of chloroethyl chloroformate are added to 0.348 mol (85 g) of 2-methyl-4-amino-5-nitro-mesyloxybenzene dissolved in 260 ml of dioxane under reflux. The heating under reflux is maintained for 4 hours, the reaction mixture is filtered whilst hot and 750g of iced water are added. The expected product crystallises. It is filtered off, washed with water and recrystallised from ethanol. Its melting point is 128° C.

Analysis of the product obtained gave the following results:

| Analysis | Calculated for $C_{11}H_{13}N_2ClSO_7$ | Found |
|---|---|---|
| C % | 37.45 | 37.65 |
| H % | 3.71 | 3.89 |
| N % | 7.94 | 8.00 |
| S % | 9.09 | 9.18 |

4th stage: Preparation of 2-methyl-4-(β-hydroxyethylamino)-5-nitro-phenol.

0.194 mol (68.5g) of β-chloroethyl N-[(2-nitro-4-mesyloxy-5-methyl)phenyl]carbamate in 190 ml of 3N potassium hydroxide solution is treated for 10 minutes on a boiling water bath. The reaction mixture is filtered whilst hot. 190 ml of 10 N potassium hydroxide solution are added to the cooled filtrate and the reaction mixture is left for 2 hours at 10° C. 2-methyl-4-(N-β-hydroxyethylamino)-5-nitro-phenol is obtained by acidifying with hydrochloric acid. The product is filtered off, washed with water and recrystallised from ethyl acetate after drying in vacuo; it melts at 174° C.

Analysis of the product obtained gave the following results:

| Analysis | Calculated for $C_9H_{12}N_2O_4$ | Found |
|---|---|---|
| C % | 50.94 | 51.09 |
| H % | 5.70 | 5.79 |
| N % | 13.20 | 13.17 |

EXAMPLE 3: Preparation of 2,6-dimethyl-4-(β-hydroxyethylamino)-3-nitro-phenol.

This process comprises four stages which are represented by the following reaction equations:

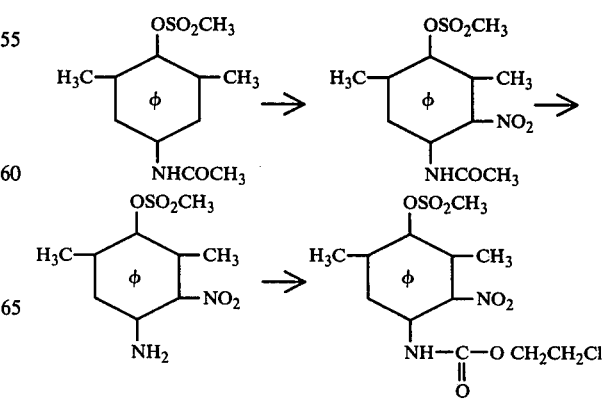

-continued

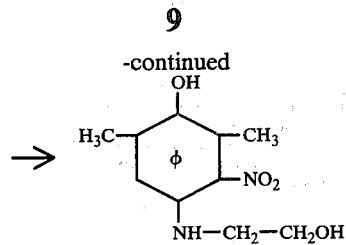

1st stage: Preparation of 2,6-dimethyl-4-acetoamino-3-nitromesyloxybenzene.

27 ml of nitric acid (d = 1.49) are added little by little, with stirring and whilst maintaining the temperature between 0° and 5° C., to 0.46 mol (118g) of 2,6-dimethyl-4-acetoamino-mesyloxybenzene (melting point = 168° C.) in 285 ml. of acetic anhydride. The stirring is maintained for 45 minutes and then the reaction mixture is poured onto 1.2 kg of crushed ice. The expected nitro derivative precipitates and this is filtered off and washed with water. After recrystallisation from ethanol, the product melts at 162° C.

Analysis of the product obtained gave the following results:

| Analysis | Calculated for $C_{11}H_{14}N_2O_6S$ | Found |
|---|---|---|
| C % | 43.71 | 43.52 |
| H % | 4.67 | 4.75 |
| N % | 9.27 | 9.14 |
| S % | 10.59 | 10.27 |

2nd stage: Preparation of 2,6-dimethyl-4-amino-3-nitromesyloxybenzene 0.265 mol (80g) of 2,6-dimethyl-4-acetoamino-3-nitromesyloxybenzene is added to a mixture of 160 ml of hydrochloric acid (d = 1.18) and 80 ml of acetic acid. After heating for two hours on a boiling water bath, 600 ml of water are added to the reaction mixture. 2,6-dimethyl-4-amino-3-nitro-phenol, which has precipitated in crystalline form, is filtered off and washed with water. After drying in vacuo, the product melts at 160° C.

3rd stage: Preparation of β-chloroethyl N-[(2-nitro-4-mesyloxy-3,5-dimethyl)phenyl]carbamate 0.2 mol (52g) of 2,6-dimethyl-4-amino-3-nitromesyloxybenzene is dissolved in 150 ml of dioxane. 0.11 mol (11g) of calcium carbonate is added and the mixture is heated to 90° C. 23 ml of chloroethylchloroformate are then added, little by little, with stirring. After heating for two hours in a boiling water bath, the reaction mixture is filtered whilst hot and then 450g of iced water are added thereto. The expected product precipitates in crystalline form. This product is filtered off, washed with water and recrystallised from ethanol. After drying in vacuo it melts at 123° C.

Analysis of the product obtained gave the following results:

| Analysis | Calculated for $C_{12}H_{15}N_2O_7ClS$ | Found |
|---|---|---|
| C % | 39.30 | 39.54 |
| H % | 4.12 | 4.41 |
| N % | 7.64 | 7.74 |
| S % | 8.74 | 9.04 |

4th stage: Preparation of 2,6-dimethyl-4-(β-hydroxyethylamino)-3-nitro-phenol 0.1 mol (36.6g) of the product obtained above in the 3rd stage is introduced into 100 ml of 3N potassium hydroxide solution. The mixture is heated for 10 minutes at 95° C. After cooling, 10 ml of 10N potassium hydroxide solution are added and the reaction mixture is left for 3 hours at ambient temperature. 2,6-Dimethyl-4-(N-β-hydroxyethylamino)-3-nitro-phenol precipitates afer neutralisation using hydrochloric acid. The product is filtered off and washed with water. After recrystallisation from ethyl acetate and drying in vacuo it melts at 160° C.

Analysis of the product obtained gave the following results:

| Analysis | Calculated for $C_{10}H_{14}N_2O_4$ | Found |
|---|---|---|
| C % | 53.09 | 53.13 |
| H % | 6.24 | 6.36 |
| N % | 12.38 | 12.32 |

EXAMPLE 4

The following dyeing composition is prepared:

| | | |
|---|---|---|
| dyestuff from Example 2 | 0.25 | g |
| monobutyl ether of ethylene glycol | 10 | g |
| ammonia of 22° B strength, q.s.p. | pH=9.5 | |
| water, q.s.p. | 100 | g |

This dyeing composition, when applied to bleached hair for 15 minutes at 25° C., imparts to the hair, after rinsing and shampooing, a "very luminous pinkish orange" coloration.

EXAMPLE 5

The following dyeing composition is prepared:

| | | |
|---|---|---|
| dyestuff from Example 2 | 0.30 | g |
| para-aminophenol | 0.10 | g |
| 2,6-dimethyl-3-methoxy-para-phenylenediamine dihydrochloride | 0.72 | g |
| 6-hydroxy-phenomorpholine | 0.60 | g |
| sodium salt of the sulphate of lauryl alcohol which has been oxyethyleneated with 2 mols of ethylene oxide, containing 19% of the oxyethyleneated lauryl alcohol starting material | 20 | g |
| ethylenediaminetetraacetic acid | 0.2 | g |
| ammonia of 22° B strength | 10 | g |
| 40% strength sodium bisulphite | 1 | g |
| water, q.s.p. | 100 | g |

At the time of the application, 100 ml of hydrogen peroxide of 20 volumes strength are added. This mixture, when applied for 20 minutes at ambient temperature to bleached hair, imparts to the hair, after rinsing and shampooing, a "deep bronze" coloration.

EXAMPLE 6

The following dyeing composition is prepared:

| | | |
|---|---|---|
| compound of Example 3 | 0.25 | g |
| monobutyl ether of ethylene glycol | 10 | g |
| ammonia of 22° B strength q.s.p. | pH=9.5 | |
| water, q.s.p. | 100 | g |

This dyeing composition, when applied for 15 minutes at 30° C. to bleached hair, imparts to the hair, after rinsing and shampooing, a "golden salmon" coloration.

EXAMPLE 7

The following dyeing composition is prepared:

| | | |
|---|---|---|
| 3-nitro-4-N-β-hydroxyethylamino-phenol | 0.25 | g |
| monobutyl ether of ethylene glycol | 5 | g |
| lauryl alcohol oxyethyleneated with 10.5 mols of ethylene oxide | 5 | g |
| ammonia of 22° B strength, q.s.p. | pH=9.5 | |
| water, q.s.p. | 100 | g |

This dyeing composition, when applied for 15 minutes at ambient temperature to bleached hair, imparts to the hair, after rinsing and shampooing, a very luminous red coloration.

EXAMPLE 8

The following dyeing composition is prepared:

| | | |
|---|---|---|
| 3-nitro-4-N-β-hydroxyethylamino-phenol | 0.1 | g |
| copolymer of vinyl acetate and crotonic acid (90% vinyl acetate, 10% crotonic acid; molecular weight = 45,000 to 50,000) | 1 | g |
| alcohol, 96° strength | 36 | g |
| water, q.s.p. | 100 | g |
| triethanolamine, q.s.p. | pH=7 | |

This dyeing composition, when applied as a wavesetting lotion to bleached hair, imparts to the hair a salmon pink coloration.

EXAMPLE 9

The following dyeing composition is prepared:

| | | |
|---|---|---|
| 3-nitro-4-N-β-hydroxyethylamino-phenol | 4 | g |
| 1-δ-aminopropylamino-anthraquinone hydrochloride | 1.5 | g |
| 3-nitro-6-amino-phenyl β-N,N-diethylaminoethyl ether | 6 | g |
| monoethyl ether of ethylene glycol | 30 | g |
| lauryl alcohol oxyetheleneated with 10.5 mols of ethylene oxide | 3.5 | g |
| ammonia of 22° B strength, q.s.p. | pH=8 | |
| water, q.s.p. | 100 | g |

This dyeing composition, when applied for 20 minutes at ambient temperature to hair which is naturally 95% white, imparts to the hair, after rinsing and shampooing, a pearlescent light chestnut coloration with a slight violine sheen.

EXAMPLE 10

The following dyeing composition is prepared:

| | | |
|---|---|---|
| 3-nitro-4-N-β-hydroxyethylamino-phenol | 0.1 | g |
| 4-nitro-3-methylamino-phenoxyethanol | 0.1 | g |
| 1-di-(β-hydroxyethyl)-amino-3-nitro-4-N-methylamino-benzene | 0.75 | g |
| nitro-meta-phenylenediamine | 0.15 | g |
| lauryl alcohol oxyethyleneated with 10.5 mols of ethylene oxide | 10 | g |
| ammonia of 22° B strength, q.s.p. | pH=8 | |
| water, q.s.p. | 100 | g |

This dyeing composition, when applied for 20 minutes at ambient temperature to bleached hair, imparts to the hair, after rinsing, and shampooing, a golden beige coloration.

EXAMPLE 11

The following dyeing composition is prepared:

| | | |
|---|---|---|
| 3-nitro-4-N-β-hydroxyethylamino-phenol | 0.20 | g |
| N-(4'-di-β-hydroxyethylamno-2'-methoxy-phenyl)-2-methyl-5-amino-benzoquinoneimine | 0.10 | g |
| 2-N-(β-hydroxyethyl)-amino-5-[4-(N,N-ethyl-acetyl-aminoethyl)-amino-anilino]-1,4-benzoquinone | 0.30 | g |
| 3-nitro-4-amino-phenol | 0.35 | g |
| polyvinylpyrrolidone (mean molecular weight 40,000) sold under Code No. K 30 by the "General Aniline and Film Corporation" | 2 | g |
| isopropanol | 25 | g |
| water, q.s.p. | 100 | g |

The final pH is 5. This dyeing composition, applied as a wavesetting lotion to bleached hair, imparts to the hair a coppery chestnut coloration.

EXAMPLE 12

The following dyeing composition is prepared:

| | | |
|---|---|---|
| 3-nitro-4-N-β-hydroxyethylamino-phenol | 0.25 | g |
| paratoluylenediamine dihydrochloride | 0.60 | g |
| 2,4-diaminoanisole dihydrochloride | 0.30 | g |
| meta-aminophenol | 0.30 | g |
| resorcinol | 0.10 | g |
| hydroquinone | 0.20 | g |
| para-aminophenol | 0.40 | g |
| 4-N-methylamino-phenol sulphate | 0.30 | g |
| ammonia of 22° B strength, q.s.p. | pH=10 | |
| oleyl alcohol oxyethyleneated with 2 mols of ethylene oxide | 3.7 | g |
| oleyl alcohol oxyethyleneated with 4 mols of ethylene oxide | 5.5 | g |
| water, q.s.p. | 100 | g |

At the time of use, 100g of hydrogen peroxide of 20 volumes strength are added to this composition. The mixture is applied for 20 minutes, at ambient temperature, to bleached hair and imparts to the hair, after rinsing and shampooing, a very dark black coloration with a violet sheen.

EXAMPLE 13

The following dyeing composition is prepared:

| | | |
|---|---|---|
| 3-nitro-4-N-β-hydroxyethylamino-phenol | 0.55 | g |
| para-toluylenediamine dihydrochloride | 0.75 | g |
| 2,5-diamino-4-methyl-phenol dihydrochloride | 0.10 | g |
| 6-hydroxy-phenomorpholine | 0.30 | g |
| α-naphthol | 0.10 | g |
| meta-aminophenol | 0.25 | g |
| monoethyl ether of ethylene glycol | 2 | g |
| carboxymethylcellulose | 4 | g |
| ammonia of 22° B strength, q.s.p. | pH=9.5 | |
| water, q.s.p. | 100 | g |

At the time of use, 60 grams of hydrogen peroxide of 20 volumes strength are added to this composition. The mixture is applied for 25 minutes at 35° C. to bleached hair and imparts to the hair, after rinsing and shampooing, a chestnut coloration with a violine sheen.

EXAMPLE 14

The following dyeing composition is prepared:

| | | |
|---|---|---|
| 3-nitro-4-N-β-hydroxyethylamino-phenol | 0.3 | g |
| 3-nitro-6-β-hydroxyethylamino-phenoxyethanol | 0.20 | g |
| 2,6-dimethyl-3-methoxy-para-phenylenediamine dihydrochloride | 0.25 | g |
| 2,4-diaminoanisole dihydrochloride | 0.15 | g |
| resorcinol | 0.20 | g |
| ammonia of 22° B strength, q.s.p. | pH=9 | |
| monomethyl ether of diethyleneglycol | 10 | g |
| water, q.s.p. | 100 | g |

At the time of use, 25g of hydrogen peroxide of 20 volumes strength are added to this composition. This mixture is applied for 10 minutes, at ambient temperature, to hair which is naturally 95% white, and imparts to the hair, after rinsing and shampooing, a golden sand coloration.

EXAMPLE 15

The following dyeing composition is prepared:

| | |
|---|---|
| 3-nitro-4-N-β-hydroxyethylamino-phenol | 0.5 g |
| 2-amino-4-methoxy-5-nitro-phenol | 0.55 g |
| 2-methyl-4-N,N-ethyl-carbamylmethyl-amino-aniline | 0.90 g |
| resorcinol | 0.95 g |
| α-naphthol | 0.20 g |
| sodium salt of the sulphate of lauryl alcohol which has been oxyethyleneated with 2 mols of ethylene oxide, containing 19% of the oxyethyleneated lauryl alcohol starting material | 20 g |
| ethylenediaminetetraacetic acid | 0.2 g |
| ammonia of 22° B strength (q.s.p. pH = 10.3) | 10 g |
| water, q.s.p. | 100 g |

At the time of use, 100 cm³ of hydrogen peroxide of 20 volumes strength are added to this composition. This mixture is applied for 20 minutes, at ambient temperature, to hair which is naturally 95% white and imparts to the hair, after rinsing and shampooing, a mahogany coloration.

EXAMPLE 16

The following dyeing composition in prepared:

| | |
|---|---|
| 3-nitro-4-N-β-hydroxyethylamino-phenol | 0.25 g |
| para-toluylenediamine dihydrochloride | 0.12 g |
| para-aminophenol | 0.15 g |
| 4-N-methylamino-phenol sulphate | 0.20 g |
| hydroquinone | 0.15 g |
| meta-aminophenol | 0.30 g |
| resorcinol | 0.10 g |
| 2,6-diamino-4-N,N-diethylamino-phenol trihydrochloride | 0.25 g |
| 6-hydroxy-phenomorpholine | 0.17 g |
| ammonia of 22° B strength, q.s.p. | pH = 10 |
| oleyl alcohol oxyethyleneated with 2 mols of ethylene oxide | 3.7 g |
| oleyl alcohol oxyethyleneated with 4 mols of ethylene oxide | 5.5 g |
| water, q.s.p. | 100 g |

At the time of use, 40g of hydrogen peroxide of 20 volumes strength are added to this composition. The mixture is applied for 20 minutes to bleached hair and imparts to the hair, after rinsing and shampooing, a golden chestnut coloration.

EXAMPLE 17

The following dyeing composition is prepared:

| | |
|---|---|
| 3-nitro-4-N-β-hydroxyethylamino-phenol | 0.05 g |
| resorcinol | 0.1 g |
| 2-methyl-5-N-β-hydroxyethylamino-phenol | 0.05 g |
| 2-methyl-4-N,N-ethyl-β-mesylaminoethyl-amino-aniline | 0.25 g |
| 2,6-diamino-4-N,N-diethylamino-phenol trihydrochloride | 0.1 g |
| sodium salt of the sulphate of lauryl alcohol which has been oxyethyleneated with 2 mols of ethylene oxide, containing 19% of the oxyethyleneated lauryl alcohol starting material | 20 g |
| ethylenediaminetetraacetic acid | 0.2 g |
| 40% strength sodium bisulphite solution | 1 g |
| ammonia of 22° B strength, q.s.p. | pH = 10 |
| water, q.s.p. | 100 g |

At the time of use, 25g of hydrogen peroxide of 20 volumes strength are added to this composition. The mixture is applied for 20 minutes at ambient temperature to bleached hair and imparts to the hair, after rinsing and shampooing, an ashen beige coloration with a pink sheen.

EXAMPLE 18

The following dyeing composition is prepared:

| | |
|---|---|
| 3-nitro-4-N-β-hydroxyethylamino-phenol | 0.20 g |
| 2,6-diamino-4-N,N-diethylamino-phenol | 0.40 g |
| 4-hydroxy-4-amino-3,5,2',5'-tetramethyl-diphenylamine | 0.15 g |
| monoethyl ether of ethylene glycol | 1.5 g |
| diethanolamide of copra fatty acid | 7.5 g |
| ammonia of 22° B strength, q.s.p. | pH = 10 |
| water, q.s.p. | 100 g |

At the time of use, 40g of hydrogen peroxide of 20 volumes strength are added to this composition. The mixture is applied for 25 minutes at 35° C. to natural hair and imparts to the hair, after rinsing and shampooing, a slightly pink pearlescent beige coloration.

EXAMPLE 19

The following dyeing composition is prepared:

| | |
|---|---|
| 3-nitro-4-N-β-hydroxyethylamino-phenol | 0.18 g |
| 1-N,N-methyl-β-hydroxyethyl-amino-3-nitro-4-N'-β-hydroxyethylamino-benzene | 0.38 g |
| 3-nitro-4-amino-phenoxyethanol | 0.21 g |
| 3-nitro-6-N-β-hydroxyethylamino-phenoxyethanol | 0.26 g |
| 2,5-diamino-4-methyl-phenol dihydrochloride | 0.05 g |
| ammonium lauryl-sulphate | 10 g |
| ammonia, q.s.p. | pH = 9 |
| water, q.s.p. | 100 g |

This dyeing composition, when applied for 20 minutes at ambient temperature to bleached hair, imparts to the hair, after rinsing and shampooing, an intense copper coloration.

EXAMPLE 20

The following dyeing composition is prepared:

| | |
|---|---|
| 3-nitro-4-N-β-hydroxyethylamino-phenol | 0.20 g |
| trihydroxybenzene | 2 g |
| para-toluylenediamine dihydrochloride | 3.10 g |
| alcohol of 96° strength | 30 g |
| water, q.s.p. | 100 g |
| triethanolamine, q.s.p. | pH = 8 |

This dyeing composition is applied for 20 minutes at ambient temperature to bleached hair. After rinsing and shampooing, a golden light chestnut coloration is obtained.

Of course the embodiments described above in no way imply a limitation and can be modified in any desirable manner without thereby going outside the scope of the invention.

We claim:

1. A dye compound having the formula $$\begin{array}{c} OH \\ R_2 \diagup \diagdown R_1 \\ | \phi | \\ \diagdown \diagup NO_2 \\ NH-CH_2CH_2OH \end{array} \quad (I)$$

in which $R_1$ and $R_2$ are identical or different and represent hydrogen or alkyl having from 1 to 4 carbon atoms.

2. Dyeing composition for keratin fibres and human hair, which comprises, in aqueous solution, at least one dye compound of claim 1.

3. Composition of claim 2, which comprises from 0.002% to 5% by weight of at least one of said dye compounds.

4. Composition of claim 2 in which the pH of the composition is between 3 and 11.

5. Composition of claim 4, in which the pH is established by ammonia, organic amines or by sodium hydrogen phosphate.

6. Composition of claim 2 which can be used as a semi-permanent dye, that additionally contains nitro dyestuffs corresponding to the general formula:

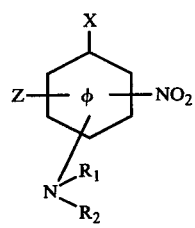

in which formula X represents hydrogen, halogen, alkyl,

or $OR_5$, with $R_1$, $R_2$, $R_3$, $R_4$ and $R_5$, which may be identical or different being hydrogen, alkyl or a substituted alkyl
and Z represents hydrogen or halogen alkyl, alkoxy or $NO_2$.

7. Composition of claim 2 which can be used in semi-permanent dyeing, which additionally contains anthraquinone dyestuffs, azo dyestuffs, oxazines, indoanilines or indophenols.

8. Composition of claim 2 which can be used as a colouring wavesetting lotion, that additionally contains, in aqueous-alcoholic solution, direct dyestuffs and at least one cosmetic resin.

9. Composition of claim 2, which can be used for obtaining permanent dyeings that additionally contains at least one oxidation dyestuff.

10. Composition of claim 9, that contains, as a mixture, at least one para-phenylenediamine or para-aminophenol oxidation base and at least one coupler.

11. Composition of claim 10, in which the oxidation base has the general formula

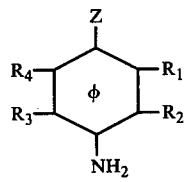

in which $R_1$, R, $R_3$ and $R_4$ are identical or different and represent hydrogen, alkyl, alkoxy or halogen, Z represents OH or

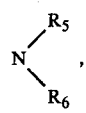

$R_5$ and $R_6$ being identical or different and representing hydrogen, alkyl or substituted alkyl, with the reservation that $R_1$ and $R_4$ represent hydrogen when $R_5$ and $R_6$ do not represent hydrogen.

12. Composition of claim 10, in which the oxidation base contains a heterocyclic nucleus.

13. Composition of claim 10 in which the couplers are chosen from the group consisting of:
(a) α-naphthol, resorcinol and its derivatives which are substituted in the nucleus,
(b) the meta-aminophenols which are substituted in the nucleus or on the amine group and which correspond to the general formula

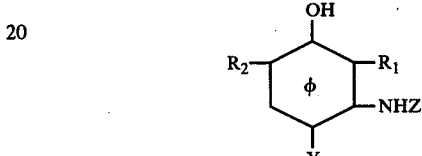

in which $R_1$ and $R_2$ can be identical or different, and represent halogen, alkoxy, alkyl or hydrogen, Y represents hydrogen, alkoxy or alkyl, and Z represents alkyl, substituted alkyl, or acyl, ureido or carbethoxy group, with the reservation that $R_2$ must be hydrogen and Z must be hydrogen or alkyl or substituted alkyl when Y is an alkyl group,
(c) the metadiamines, which can have substituents in the nucleus or on the amine group,
(d) the couplers which comprise a pyridine nucleus and
(e) the couplers of the group of pyrazolones, β-diketones and 6-hydroxy-phenomorpholine.

14. Composition of claim 2 that additionally contains at least one hair dyestuff which can undergo auto-oxidation.

15. Composition of claim 2 that additionally contains at least one product chosen from the group consisting of:
(a) solvents other than water,
(b) anionic, cationic or non-ionic surface-active agents, sulphonated esters of alcohol, sulphates of fatty alcohols and sodium lauryl sulphate,
(c) thickening agents,
(d) antioxydants,
(e) sequestring agents and
(f) perfumes.

16. Process of producing the compounds of claim 1, comprising reacting chloroethyl chloroformate with 3-nitro-4-amino-phenol, which is optionally substituted in the 2- and/or 6-position(s) by an alkyl radical having from 1 to 4 carbon atoms, the reaction taking place in dioxane in the presence of calcium carbonate, and in that an alkaline hydrolysis of the carbamate formed is carried out thereafter.

17. Process of claim 16, which the reaction with the chloroethyl chloroformate takes place at a temperature of between about 70 and 100° C.

18. Process of claim 16 in which the alkaline hydrolysis of the carbamate formed is carried out with a concentrated aqueous potassium hydroxide solution, at a temperature of between 0 and 25° C.

19. The compound of claim 1, which is 3-nitro-4-(β-hydroxyethylamino)-phenol.

20. The compound of claim 1, which is 2-methyl-4-(β-hydroxyethylamino)-5-nitro-phenol.

21. The compound of claim 1, which is 2,6-dimethyl-4-(β-hydroxyethylamino)-3-nitro-phenol.

* * * * *